United States Patent
Lee et al.

(10) Patent No.: US 9,574,875 B2
(45) Date of Patent: Feb. 21, 2017

(54) WAFER OR RETICLE THERMAL DEFORMATION MEASURING TECHNIQUES

(71) Applicant: Taiwan Semiconductor Manufacturing Co., Ltd., Hsin-Chu (TW)

(72) Inventors: Tsung-Hsun Lee, Kaohsiung (TW); Kai-Fa Ho, New Taipei (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 260 days.

(21) Appl. No.: 14/159,604

(22) Filed: Jan. 21, 2014

(65) Prior Publication Data

US 2015/0204665 A1    Jul. 23, 2015

(51) Int. Cl.
*G01N 19/00* (2006.01)
*G01B 21/32* (2006.01)
*G01N 25/16* (2006.01)

(52) U.S. Cl.
CPC ............... *G01B 21/32* (2013.01); *G01N 25/16* (2013.01)

(58) Field of Classification Search
CPC .................................. G01B 21/32; G01N 25/16
USPC ............................................ 374/55; 73/865.9
See application file for complete search history.

(56) References Cited

U.S. PATENT DOCUMENTS

| | | | |
|---|---|---|---|
| 7,025,280 B2 * | 4/2006 | Kaushal | G03F 1/144 118/50.1 |
| 2012/0120379 A1 * | 5/2012 | Phillips | F28F 3/12 355/52 |
| 2012/0267550 A1 | 10/2012 | Donders et al. | |
| 2013/0038321 A1 | 2/2013 | Suzuki | |

* cited by examiner

*Primary Examiner* — John Fitzgerald
*Assistant Examiner* — Rodney T Frank
(74) *Attorney, Agent, or Firm* — Eschweiler & Associates, LLC (57) ABSTRACT

A system includes a wafer stage adapted to hold a semiconductor wafer thereon. A moveable temperature sensor array is configured to move to a plurality of different positions over a surface of the wafer stage and to take a plurality of temperature measurements at the plurality of positions, respectively. Based on the plurality of temperature measurements, a controller is adapted to determine an expected thermal deformation for the semiconductor wafer or for a reticle arranged over the semiconductor wafer.

19 Claims, 5 Drawing Sheets

WAFER OR RETICLE THERMAL DEFORMATION MEASURING TECHNIQUES

BACKGROUND

Over the last four decades, the density of integrated circuits has increased by a relation known as Moore's law. Stated simply, Moore's law says that the number of transistors on integrated circuits (ICs) doubles approximately every 18 months. Thus, as long as the semiconductor industry can continue to uphold this simple "law," ICs double in speed and power approximately every 18 months. In large part, this remarkable increase in the speed and power of ICs has ushered in the dawn of today's information age.

Unlike laws of nature, which hold true regardless of mankind's activities, Moore's law only holds true only so long as innovators can continue to overcome the technological challenges associated with it. Improvements in optical overlay metrology, which allows extremely accurate overlay measurements to be performed between patterned layers on an IC, are being continuingly developed to allow Moore's law to continue to hold true. Optical overlay metrology can measure how accurately an overlying patterned layer, such as a photoresist layer, aligns with respect to an underlying patterned layer, such as a dielectric or metal layer, for example. If a workpiece contains layers that are misaligned, then the misaligned layers can be re-worked to correct the misalignment. For example, a misaligned photoresist layer can be stripped, and a new layer of photoresist can be applied and re-exposed at a corrected alignment, thereby enabling precise alignment of IC features.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

As geometries continue to shrink, obtaining extremely precise alignments between layers on an IC becomes more and more important. Alignment marks are used to measure overlay offset between patterned layers on a semiconductor workpiece. The most commonly used overlay alignment marks are squares, generally referred to as "bar-in-bar" marks, some examples of which are shown in FIGS. 1A-1D. FIGS. 1A-1D each show a top view of bar-in-bar mark 100 having inner and outer bar marks 102, 104, respectively, disposed on upper and lower layers, respectively. For example, lower layer on which outer bar mark 104 is formed could be a semiconductor substrate, a metal layer, a dielectric layer, or any other layer or layers; while the upper layer on which inner bar mark 102 is formed could be a photoresist layer or other mask layer, for example. Although bar-in-bar alignment marks are discussed herein for purposes of explanation, it will be appreciated that a vast assortment of other alignment marks could also be used, and the present disclosure is in no way limited to bar-in-bar alignment marks.

Figure 1A:
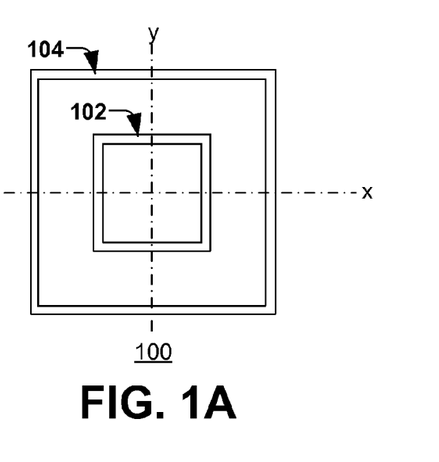
FIGS. 1A-1D illustrate top views of alignments marks which suffer from overlay offset.

FIG. 1A shows a top view of bar-in-bar mark 100, where the inner and outer bar marks 102, 104 have zero overlay-offset. This means that the inner bar mark 102, which is for example formed on an upper photoresist layer, when viewed through a microscope, appears to be exactly centered within the lower outer bar mark 104, which is for example formed on an underlying dielectric or metal layer. Thus, as evidenced by marks 102, 104 in FIG. 1A, the upper and lower layers in FIG. 1A appear to be perfectly aligned when viewed.

Figure 1B:
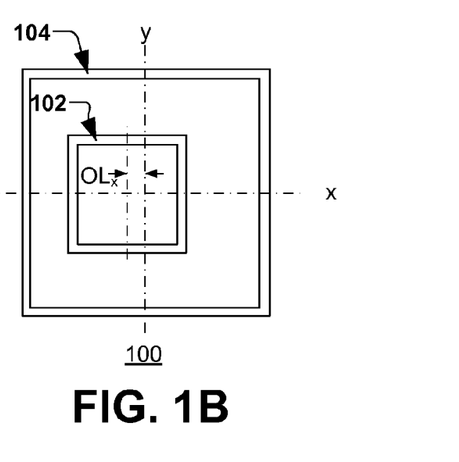
Figure 1C:
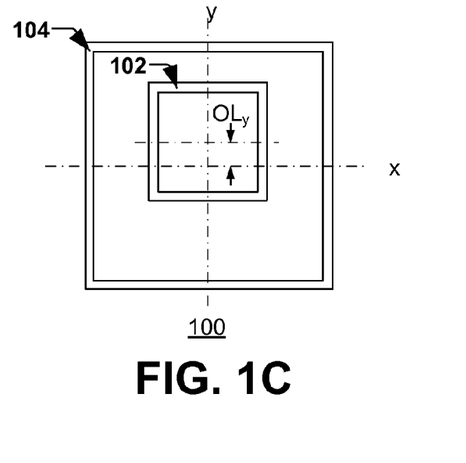
Figure 1D:
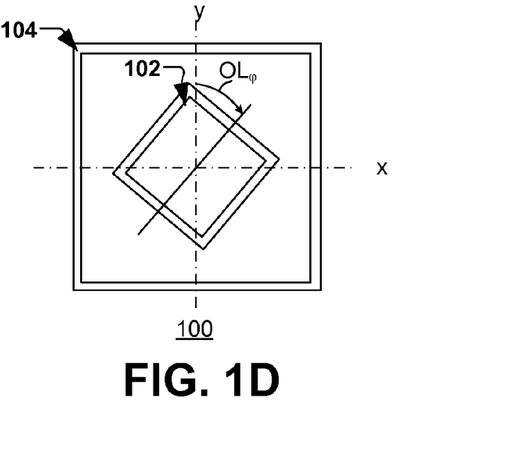

Although FIG. 1A shows an example where the layers are aligned with one another, the layers can in practical situations have offsets by which they are misaligned. For example, FIG. 1B shows an example of an overlay overset in the X-direction (see $OL_x$, wherein the upper layer is undesirably shifted to the left by an amount $OL_x$), and FIG. 1C shows an example of an overlay-offset in the Y-direction (see $OL_y$, wherein the upper layer is undesirably shifted upwards by an amount $OL_y$). There can also be skew or rotation between the layers, as shown in FIG. 1D (see $OL_\phi$ in FIG. 1D, wherein the upper layer is undesirably rotated by an amount $OL_{100}$). Ideally, each alignment mark on a wafer would be perfectly aligned as shown in FIG. 1A, however, in real-world situations there is some amount of misalignment which can be a combination of one or more of these offsets.

Figure 2:
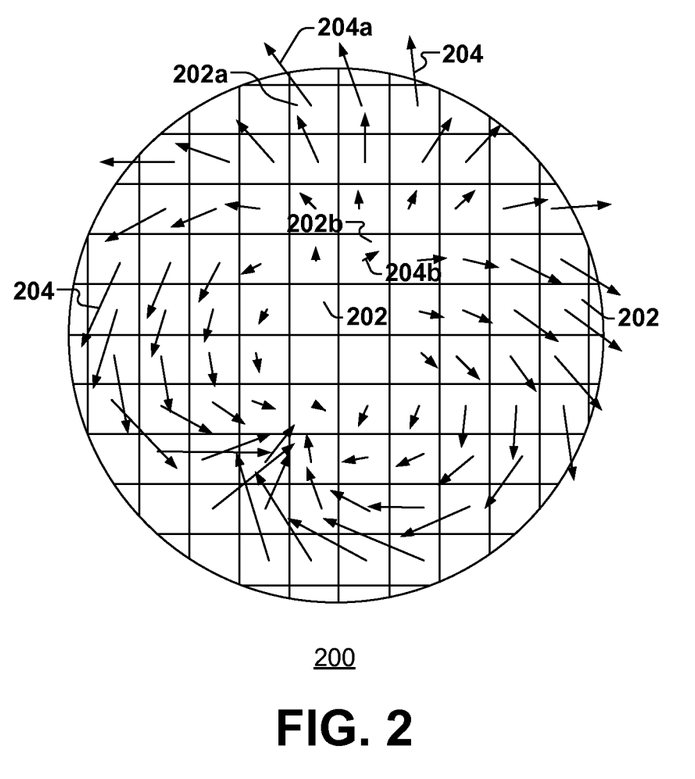
FIG. 2 illustrates a wafer made up of die having corresponding overlay offset vectors superimposed thereon, wherein the overlay offset vectors may be due to reticle and/or wafer temperature variations during processing.

As shown in FIG. 2, with regards to a semiconductor wafer 200, which includes an array of die 202 arranged in grid-like fashion over a face thereof, misalignment or overlay offset can be different for different dies on the wafer. In particular, FIG. 2 shows misalignment vectors 204 superimposed on the respective dies 202. In the illustrated example, each misalignment vector has a direction that is a superposition of x-overlay offset and y-overlay offset for two uppermost layers on a given die, and has a magnitude corresponding to the amount of misalignment between the two layers for that die. Thus, a die with a longer misalignment vector, e.g., die 202a with misalignment vector 204a, tends to have its two uppermost layers more misaligned than a die with a shorter misalignment vector, e.g., die 202b with misalignment vector 204b. In this example, dies positioned near the wafer's center tend to have smaller misalignment than dies positioned closer to the wafer's outer edge.

One underlying cause of this variation in misalignment over the wafer 200 is localized thermal distortion of the wafer 200 during processing, which can result in volumetric or thermal expansion or contraction of some wafer regions relative to other wafer regions. For example, when light, which passes through a reticle to impinge on a die region 202, initially strikes the die to form a lithographic pattern thereon, the wafer may initially exhibit one temperature gradient pattern due to the light causing un-even heating over the wafer's surface. Therefore, even if the pattern provided by this lithographic pattern is "perfect" when first patterned, when the wafer is subsequently removed from the lithography system, the wafer may "cool off" or "heat up" such that the patterned lithographic features may now end up being thermally distorted from the initially imprinted "perfect" lithographic pattern, due to local temperature variations on wafer 200. Similarly, as light passes through a reticle, the reticle itself can experience local thermal deformations, and thus its imaging characteristics can change due to thermal deformation. These localized thermal distortion effects can lead to corresponding translational or rotational distortion for patterns imprinted on the wafer.

Although some conventional approaches may attempt to make provide temperature profiling for reticles during lithography, the temperature sensors used in these approaches have remained fixed in place out throughout lithography. Thus, in these approaches, the reticle must be moved out of the illumination path to have its temperature profile measured, and then the reticle must be moved back onto the illumination path after the temperature profile has been measured for a photolithographic exposure to occur. This movement can cause the temperature profile which is measured for the reticle to deviate from the temperature profile present when the reticle actually undergoes lithographic exposure. Hence, due to changes in temperature, there can be reticle distortion that is not accurately accounted for. In addition, movement of the reticle can cause misalignment due to mechanical tolerances, which can add to misalignment of layers.

Accordingly, the present disclosure relates to techniques for measuring wafer and/or reticle thermal deformation. In particular, the techniques provided herein provide a moveable temperature sensor that can measure a temperature profile for a reticle and/or wafer. This moveable temperature sensor can provide more accurate temperature profile measurements than previously achievable.

Figure 3:
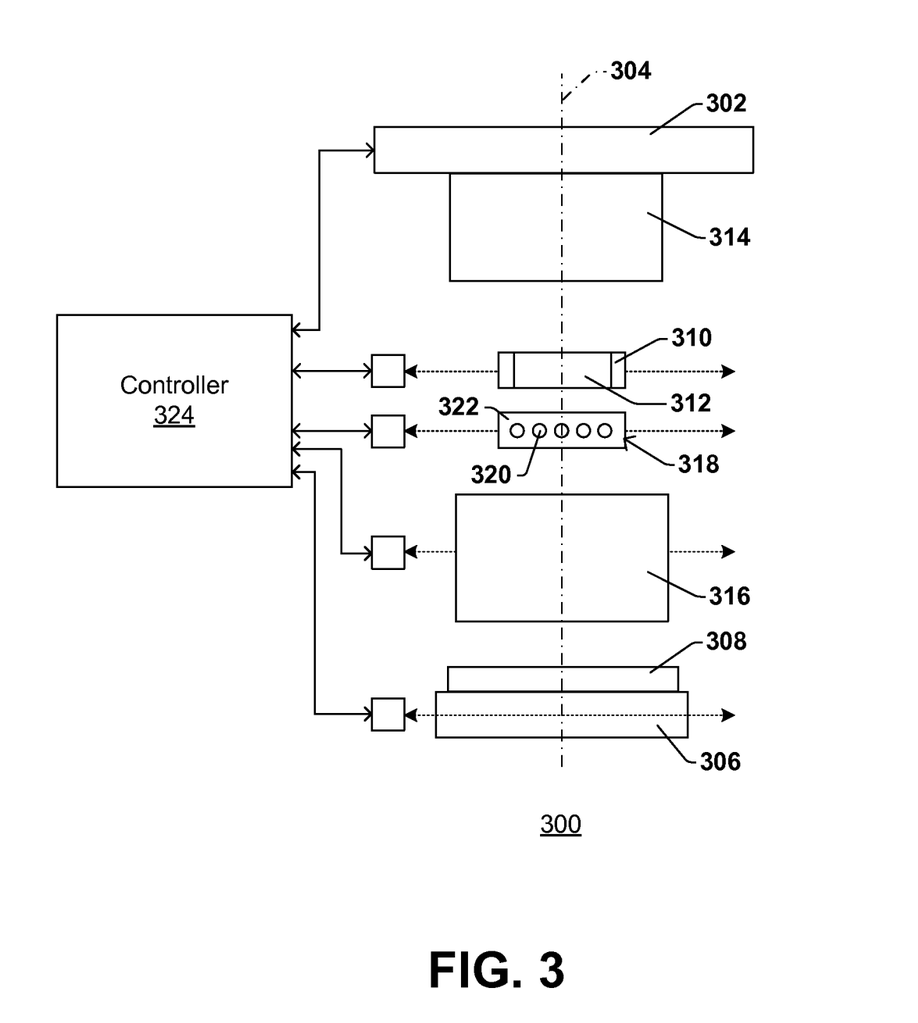
FIG. 3 illustrates a semiconductor processing system that includes a moveable temperature sensor array in accordance with some embodiments.

FIG. 3 shows an example of a semiconductor processing system 300 in accordance with some embodiments. The system 300 includes an illumination source 302 adapted to provide light along an optical axis 304 which intersects a location on a moveable wafer stage 306 where a wafer 308 is to reside. A reticle stage 310 is selectively aligned on the optical axis 304 and adapted to hold a reticle 312 thereon. When light from the illumination source 302 passes through first optical assembly 314, through reticle 312, and through second optical assembly 316, a reticle image is formed on the semiconductor wafer 308. This reticle image can be imprinted on a photoresist layer on wafer 308, which allows the reticle image to be transferred onto the wafer 308.

To help ensure the reticle image is accurately aligned and/or has accurate feature shapes, the system 300 includes a moveable temperature sensor array 318. The moveable temperature sensor array 318, which includes a number of temperature sensor elements 320 on a mounting element 322, is configured to move to a plurality of different positions over a surface of the wafer 308 and/or reticle 312 under the direction of controller 324, and is further configured to take a plurality of temperature measurements at the plurality of positions, respectively. Based on the plurality of temperature measurements, the controller 324 can determine a temperature profile and expected thermal deformation of the wafer 308 and/or reticle 312 so appropriate countermeasures can be taken.

In some embodiments, the wafer stage 306, reticle stage 310, and/or optical assemblies 314, 316 may be fixed in position to help limit misalignment. The wafer stage 306, reticle stage 310, and temperature sensor array 318 are configured to each be aligned on the optical axis 304 so the moveable temperature sensor array 318 can determine a first temperature gradient profile for the wafer 308 and a second temperature gradient profile for the reticle 312.

In other embodiments, the wafer stage 306, reticle stage 310, and/or optical assemblies 314, 316 may be fixed in position to help limit misalignment. In some instances, the second optical assembly 316 is movable. In particular, the second optical assembly can selectively move from a first optical assembly position off the optical axis 304 to a second optical assembly position on the optical axis 304 under direction of controller 324. In some instances when the second optical assembly 316 is positioned off optical axis 304, the moveable temperature sensor array 318 can concurrently take thermal profiles for the wafer 308 and the reticle 310.

Figure 4A:
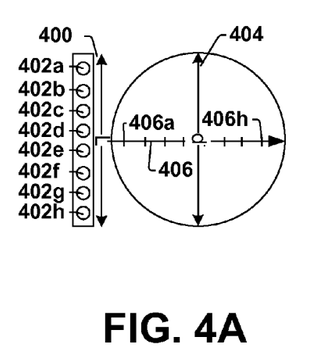
FIGS. 4A-4C illustrate top views depicting some examples of how a moveable temperature sensor array can move in accordance with some embodiments.
Figure 4B:
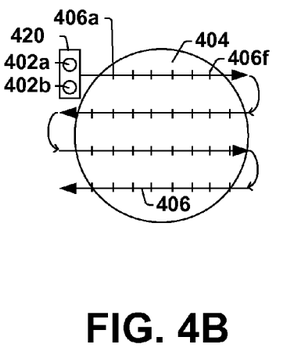
Figure 4C:
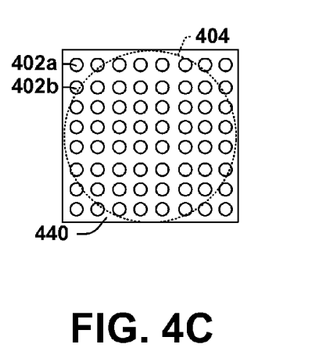

FIGS. 4A-4C show top views of various types of movement that can be performed by FIG. 3A's moveable temperature sensor array 318 to measure a temperature profile in accordance with some embodiments. FIG. 4A shows an example of a moveable temperature sensor array 400 that includes a number of temperature sensor elements (e.g., 402a, . . . , 402h), which are spaced over a length, L, that is approximately equal to a wafer diameter, d, or maximum length of reticle (not shown). In FIG. 4A's embodiment, the moveable temperature sensor array 400 can profile the temperature of the entire wafer 404 and/or entire reticle by taking a series of temperature measurements over a number of positions (e.g., 406a, . . . , 406h) on a single linear scan path 406. The temperature sensor elements (e.g., 402a, . . . , 402h) can comprise infrared photodiodes in some embodiments.

In other instances, such as shown in FIG. 4B, moveable temperature sensor array 420 can contain fewer temperature sensor elements that are spaced at a length that is less than the wafer diameter d, and/or less than the maximum reticle length. In this implementation, the temperature sensor array 420 scans an individual linear segment (e.g., row) of the wafer, then moves to the next adjacent linear segment and scans it, and so on, until the entire surface of the wafer is scanned.

Further, as shown in FIG. 4C in still other instances, temperature sensor array 440 can have a sufficiently large number of diodes that an area imaged by the temperature sensor array at a given instant corresponds to an entire wafer area bounded by a circumferential edge of the wafer 404. Each of these temperature sensor arrays in FIGS. 4A-4C gives different tradeoffs between accurate temperature profile measurements and cost.

In some embodiments, the wafer and/or reticle can be thermally imaged completely prior to the photolithography being carried out. However, in other embodiments, such as in FIG. 4B, the moveable temperature sensor array 420 and reticle can be stepped concurrently in coordinated fashion throughout photolithography. For example, in some embodiments where only the wafer is thermally imaged (i.e., reticle is not thermally imaged), the thermal sensor array 420 can take a thermal image of one die location, and as the thermal sensor array moves onto the next die location, the reticle can be positioned over the previous die location and form a reticle image on that die location. Thus, the reticle can "trail behind" the thermal sensor array in locked, step-wise fashion throughout thermal profiling and lithography. In other embodiments where the wafer and reticle are both thermally imaged, the temperature sensor array 420 can be arranged under the reticle and over the die location (e.g., as shown in FIG. 3), then thermal images for the reticle and die location can be taken concurrently, and then the reticle can be moved to over the next die location and the photolithography for the die location can carried out. In other embodiments, the temperature sensor array can thermally image a die location, then scan back and thermally image the reticle arranged over a previous die location; and then move forward back over the die location while the thermally-imaged reticle images the previous die location. Other types of coordinated movement are also possible.

Figure 5:
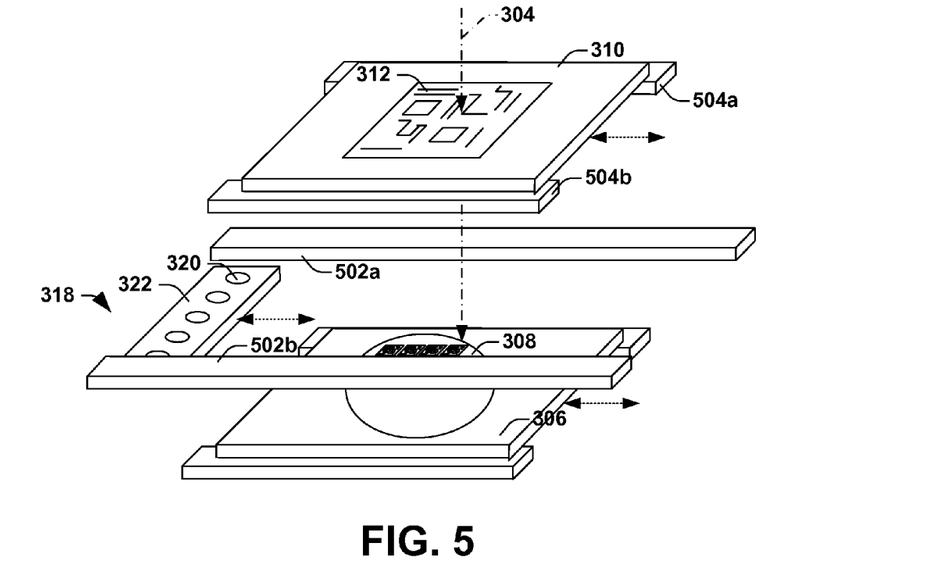
FIG. 5 illustrates a semiconductor processing system that includes a moveable temperature sensor in accordance with some embodiments.

As shown in FIG. 5, to provide suitable movement, the moveable temperature sensor array 318 includes a first pair of parallel rails 502a, 502b, which extend over the wafer stage 306 and wafer 308. A mounting element 322, which engages the pair of parallel rails, moves along the pair of parallel rails to move between the plurality of different positions under direction of a controller. An array of temperature sensors 320a are mounted on the mounting element 322 and are adapted to take temperature measurements under direction of the controller.

As shown in FIG. 5, the reticle stage 310 can be supported by a pair of parallel rails 504a, 504b, which extend over the wafer stage 306 and wafer 308. The reticle stage engages the pair of parallel rails 504a, 504b, and has an reticle engagement surface to receive the reticle. The reticle stage 310 is moveable along these rails 504a, 504b under direction of a controller.

Figure 6:
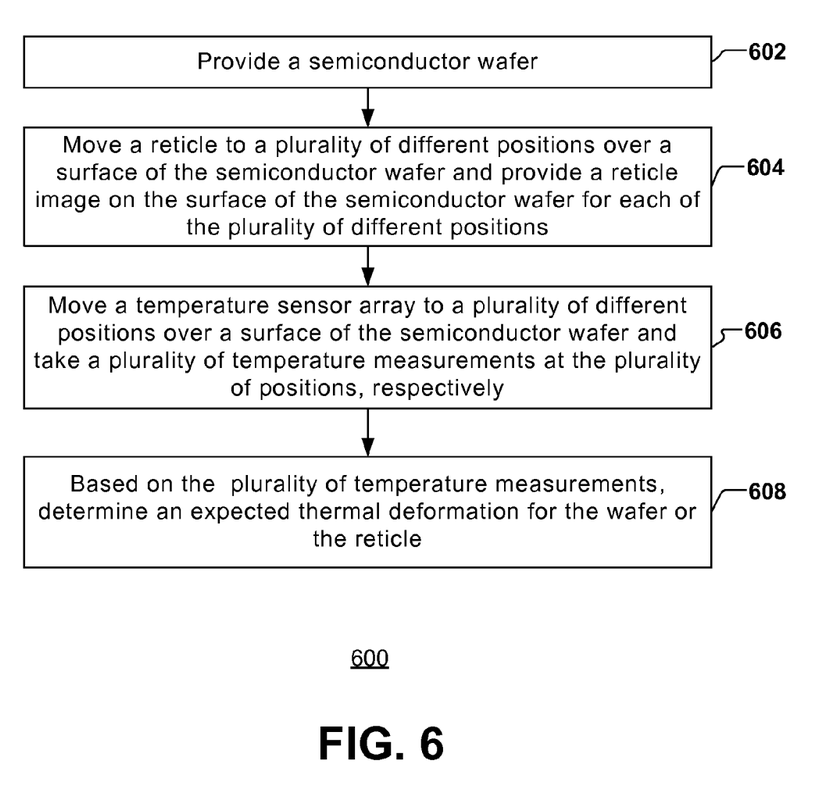
FIG. 6 illustrates a method in flowchart form that makes use of a moveable temperature sensor in accordance with some embodiments.

FIG. 6 shows a methodology 600 in flowchart format in accordance with some embodiments. In this methodology, a semiconductor wafer is provided in 602.

In 604, a reticle is moved to a plurality of different positions over a surface of the semiconductor wafer and a reticle image is provided on the surface of the semiconductor wafer for each of the plurality of different positions.

In 606, a temperature sensor array is moved to a plurality of different positions over a surface of the semiconductor wafer and a plurality of temperature measurements are taken at the plurality of positions, respectively.

At 608, based on the plurality of temperature measurements, an expected thermal deformation for the wafer and/or the reticle is determined.

Although some embodiments have been described above in the context of a lithography system (see e.g., FIG. 3), moveable temperature sensor arrays as provided herein are not limited to lithography systems and can be used with a chemical vapor deposition (CVD) or physical vapor deposition (PVD) element as well. In these embodiments, the controller is configured to tune deposition characteristics of the CVD or PVD element based on the determined thermal gradient profile. For example, the controller can provided localized heating or cooling of the wafer through a heating element with multiple heating elements spread over different areas of the wafer to offset the determined thermal gradient profile to provide a uniform temperature over the entire wafer. If present, in some embodiments, the CVD or PVD element can be included in addition to the reticle, optical assembly, and illumination source. In other embodiments, however, the CVD or PVD element can be included solely with the moveable temperature sensor array, wafer stage, and controller, and enclosed in a vacuum chamber without the photolithography elements described in FIG. 3. Thus, depending on the implementation, the movable temperature sensor array can be used in the context of photolithography to account for wafer and/or reticle deformation; or can be used in the context of other processing steps such as PVD or CVD to help ensure temperature dependent steps are carried out uniformly across surface of wafer.

Accordingly, as described above, the present disclosure relates to techniques for measuring wafer and/or reticle thermal deformation. In particular, the techniques provided herein provide a moveable temperature sensor that can measure a temperature profile for a reticle and/or wafer. This moveable temperature sensor can provide more accurate temperature profile measurements than previously achievable.

Some embodiments relate to a system which includes a wafer stage adapted to hold a semiconductor wafer thereon. A moveable temperature sensor array is configured to move to a plurality of different positions over a surface of the wafer stage and to take a plurality of temperature measurements at the plurality of positions, respectively. Based on the plurality of temperature measurements, a controller is adapted to determine an expected thermal deformation.

Other embodiments relate to a system which includes a wafer stage adapted to hold a semiconductor wafer thereon. An illumination source provides light along an optical axis such that the light strikes the wafer stage at a location at which the semiconductor wafer is to be held. A moveable reticle stage selectively moves a reticle from a first reticle position off the optical axis to a second position on the optical axis. An optical assembly focuses light that has passed through the reticle onto the location on the wafer stage where the wafer is to be held. A moveable temperature sensor array moves to a plurality of different positions over a surface of the wafer stage and takes a plurality of temperature measurements at the plurality of positions, respectively. Based on the plurality of temperature measurements, a controller determines an expected thermal deformation for the reticle or the semiconductor wafer.

Still other embodiments relate to a method. In the method, a semiconductor wafer is provided. A reticle is moved to a plurality of different positions over a surface of the semiconductor wafer. A reticle image is provided on the surface of the semiconductor wafer for each of the plurality of different positions. A temperature sensor array is moved to a plurality of different positions over a surface of the semiconductor wafer and a plurality of temperature measurements are taken at the plurality of positions, respectively. Based on the plurality of temperature measurements, an expected thermal deformation is determined for the wafer or the reticle.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A system, comprising:
   a wafer stage adapted to hold a semiconductor wafer thereon;
   a first pair of parallel rails which extend over the wafer stage;
   a mounting element that engages the first pair of parallel rails and which is configured to move between a plurality of different positions along the first pair of parallel rails;
   a moveable array of temperature sensors mounted on the mounting element and configured to take a plurality of temperature measurements at the plurality of different positions, respectively; and
   a controller adapted to direct the mounting element to move between the plurality of different positions and to direct the moveable array of temperature sensors to take the plurality of temperature measurements, wherein the controller is further adapted to, based on the plurality of temperature measurements, determine an expected thermal deformation for the semiconductor wafer or for a reticle arranged over the semiconductor wafer.

2. The system of claim 1, wherein the moveable array of temperature sensors comprises a plurality of infrared photo diodes to detect thermal radiation.

3. The system of claim 1, further comprising:
   a chemical vapor deposition (CVD) or physical vapor deposition (PVD) element; and
   wherein the controller is configured to tune deposition characteristics of the CVD or PVD element based on the plurality of temperature measurements.

4. The system of claim 1, further comprising:
   an illumination source adapted to provide light along an optical axis, wherein the optical axis intersects a location on the wafer stage at which the semiconductor wafer is to be held; and
   a reticle stage aligned on the optical axis and adapted to hold the reticle thereon, wherein the reticle and the illumination source collectively provide a reticle image at a location near the wafer stage where the semiconductor wafer is to be held;
   wherein the controller is adapted to determine a temperature gradient profile and corresponding thermal deformation for the reticle based on the plurality of temperature measurements.

5. The system of claim 4, wherein the reticle stage is moveable under direction of the controller and comprises:
   a second pair of parallel rails which extend over the wafer stage; and
   a reticle mounting element which engages the second pair of parallel rails and which is configured to receive the reticle thereon.

6. The system of claim 4, wherein the wafer stage, reticle stage, and the moveable array of temperature sensors are configured to be concurrently aligned on the optical axis so the moveable array of temperature sensors can determine a first temperature gradient profile for the wafer and a second temperature gradient profile for the reticle while in concurrent alignment.

7. The system of claim 4, wherein the reticle and the moveable array of temperature sensors are moved concurrently in coordinated fashion.

8. The system of claim 4, further comprising:
   a moveable optical assembly configured to selectively move from a first optical assembly position off the optical axis to a second optical assembly position on the optical axis under direction of the controller, wherein the moveable optical assembly is configured to focus light that has passed through the reticle onto a location on the wafer stage where the semiconductor wafer is to be held.

9. The system of claim 8, wherein the wafer stage, the reticle stage, and the moveable array of temperature sensors are configured to be concurrently at least substantially aligned on the optical axis while the moveable optical assembly is off the optical axis so the moveable array of temperature sensors can concurrently determine a first temperature gradient profile for the semiconductor wafer and a second temperature gradient profile for the reticle.

10. A system, comprising:
    a wafer stage adapted to hold a semiconductor wafer thereon;
    an illumination source adapted to provide light along an optical axis, wherein the light is to strike the wafer stage at a location at which the semiconductor wafer is to be held;
    a moveable reticle stage configured to selectively move a reticle from a first reticle position off the optical axis to a second position on the optical axis;
    an optical assembly configured to focus light that has passed through the reticle onto a location on the wafer stage where the semiconductor wafer is to be held;
    a moveable temperature sensor array configured to move independently of the moveable reticle stage to a plurality of different positions over a surface of the wafer stage and to take a plurality of temperature measurements at the plurality of positions, respectively; and
    a controller adapted to, based on the plurality of temperature measurements, determine an expected thermal deformation for the reticle or the semiconductor wafer.

11. The system of claim 10, wherein the optical assembly is configured to selectively move from a first optical assembly position off the optical axis to a second optical assembly position on the optical axis under direction of the controller.

12. The system of claim 11, wherein the wafer stage, the moveable reticle stage, and the moveable temperature sensor array are configured to be concurrently at least substantially aligned on the optical axis while the optical assembly is off the optical axis so the moveable temperature sensor array can determine a first temperature gradient profile for the wafer and a second temperature gradient profile for the reticle.

13. The system of claim 10, wherein the moveable temperature sensor array comprises:
    a first pair of parallel rails which extend over the wafer stage;
    a mounting element that engages the first pair of parallel rails and which moves along the first pair of parallel rails to move between the plurality of different positions under direction of the controller; and
    an array of temperature sensors mounted on the mounting element and adapted to take temperature measurements under direction of the controller.

14. The system of claim 10, wherein the reticle stage is moveable under direction of the controller and comprises:
- a second pair of parallel rails which extend over the wafer stage; and
- a reticle mounting element which engages the second pair of parallel rails and which is configured to receive the reticle thereon.

15. The system of claim 14, wherein the reticle and temperature sensor array are moved concurrently in coordinated fashion.

16. A method, comprising:
providing a semiconductor wafer;
moving a reticle to a plurality of different reticle positions over a surface of the semiconductor wafer and providing a reticle image on the surface of the semiconductor wafer for each of the plurality of different reticle positions;
moving a temperature sensor array to a plurality of different sensor positions over a surface of the semiconductor wafer and taking a plurality of temperature measurements at the plurality of sensor positions, respectively, wherein the reticle and the temperature sensor array are moved concurrently in coordinated fashion; and
based on the plurality of temperature measurements, determining an expected thermal deformation for the semiconductor wafer or the reticle.

17. The method of claim 16, wherein the temperature sensor array includes a plurality of temperature sensor elements that are spread over a length that is approximately equal to a diameter of the semiconductor wafer.

18. The method of claim 16, wherein the temperature sensor array moves to the plurality of different positions independently of the reticle.

19. The method of claim 16, further comprising:
performing a chemical vapor deposition (CVD) or physical vapor deposition (PVD) in which a deposition characteristic of the CVD or PVD is tuned based on the plurality of temperature measurements.

* * * * *